United States Patent [19]
Haslanger et al.

[11] Patent Number: 4,801,609
[45] Date of Patent: Jan. 31, 1989

[54] MERCAPTO-ACYLAMINO ACID ANTIHYPERTENSIVES

[75] Inventors: Martin F. Haslanger, Ridgewood; Bernard R. Neustadt, West Orange; Elizabeth M. Smith, Verona, all of N.J.

[73] Assignee: Schering Corporation, Kenilworth, N.J.

[21] Appl. No.: 32,153

[22] Filed: Mar. 27, 1987

[51] Int. Cl.$^4$ .................. C07C 103/00; C07C 149/40; C07C 149/43; C07C 147/107

[52] U.S. Cl. .................................. 514/506; 558/254; 558/417; 564/153; 564/154; 560/10; 560/16; 560/17; 560/18; 562/426; 562/427; 562/432; 514/522; 514/513; 514/529; 514/532; 514/540; 514/562

[58] Field of Search ................ 558/254, 417; 564/153, 564/154; 560/10, 16, 17, 18; 562/426, 427, 432; 514/522, 506, 513, 529, 532, 540, 562

[56] References Cited

U.S. PATENT DOCUMENTS 4,053,651 10/1977 Ondetti et al. ...................... 558/254
4,329,495 5/1982 Bindra ................................ 564/153
4,401,677 4/1983 Greenberg et al. ................ 564/153
4,513,009 4/1985 Roques et al. ...................... 558/254
4,740,499 4/1988 Olins .................................... 530/300

FOREIGN PATENT DOCUMENTS 0038046 10/1981 European Pat. Off. ........... 558/254
136883 4/1985 European Pat. Off. ........... 564/153

OTHER PUBLICATIONS

Griffith, Ann. Rev. Biochem., 1986, pp. 855–878.
Needleman et al, *N. Eng. J. Med.*, 314, 13 (1986) pp. 828–834.
Cantin et al, *Scientific American*, 254 (1986) pp. 76–81.

*Primary Examiner*—Alan L. Rotman
*Assistant Examiner*—Robert C. Whittenbaugh
*Attorney, Agent, or Firm*—Anita W. Magatti; James R. Nelson; Stephen I. Miller

[57] ABSTRACT

Novel mercapto-acylamino acids useful in the treatment of hypertension and combinations of mercapto-acylamino acids and atrial natriuretic peptides useful for treating hypertension are disclosed.

17 Claims, No Drawings

MERCAPTO-ACYLAMINO ACID ANTIHYPERTENSIVES

SUMMARY OF THE INVENTION

The present invention relates to mercapto-acylamino acids useful in the treatment of hypertension and congestive heart failure.

The invention also relates to the treatment of hypertension and congestive heart failure with a combination of a mercapto-acylamino acid and an atrial natriuretic peptide.

Other aspects of the invention relate to pharmaceutical compositions comprising the mercapto-acylamino acids of this invention, alone or in combination with atrial natriuretic peptides, and to methods of treatment of hypertension and congestive heart failure comprising administering a mercapto-acylamino acid of this invention, alone or in combination with an atrial natriuretic peptide, to a mammal in need of such treatment.

BACKGROUND OF THE INVENTION

Human hypertension represents a disease of multiple etiologies. Included among these is a sodium and volume dependent low renin form of hypertension. Drugs that act to control one aspect of hypertension will not necessarily be effective in controlling another.

A variety of mercapto-acylamino acids are known as enkephalinase inhibitors useful as analgesics and in the treatment of hypertension.

U.S. Pat. No. 4,513,009 to Roques et al discloses, inter alia, compounds of the formula.

$$\text{HS}-\text{CH}_2-\text{CH}_2-\text{CO}-\text{NH}-\underset{\underset{\text{COOH}}{|}}{\text{CH}}-\text{COOH}$$
with $\overset{R^1}{\underset{|}{(CH_2)_n}}$ on the middle carbon and $R^2$ on the CH.

wherein n is 0 to 1; $R^1$ includes hydrogen, optionally substituted alkyl, optionally substituted phenyl, cyclohexyl and thienyl; and $R^2$ includes hydrogen optionally substituted alkyl, optionally substituted benzyl, phenyl, phenoxyalkyl and optionally substituted mercaptoalkyl. The compounds are disclosed as principally having enkephalinase activity, but also are said to be antihypertensives.

U.S. Pat. No.4,401,677 to Greenberg et al discloses compounds of a scope similar to Roques et al as having analgesic activity, while U.S. Pat. No. 4,053,651 to Ondetti et al discloses the use of similar compounds in the treatment of renin-angiotensin related hypertension.

It has recently been discovered that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homeostasis", *N. Engl. J. Med.*, 314, 13 (1986) pp. 828–834, and M. Cantin et al in "The Heart as an Endocrine Gland", *Scientific American*, 254 (1986) pg. 76–81.

DETAILED DESCRIPTION

Novel antihypertensive compounds of the present invention are represented by the following formulae:

Structures I, II, III (mercapto-acylamino acid derivatives with QS–, $(CH_2)_n$, $R^1$/$R^{1a}$, $R^2$/$R^{2a}$, $R^3$/$R^{3a}$ substituents).

wherein $R^1$ is phenyl substituted by one or more substituents independently selected from alkyl, alkoxy, cycloalkyl, cyano and aminomethyl, $Y-C_6H_4S-$, $Y-C_6H_4O-$,

[biphenyl structure with Y and X substituents]

α-naphthyl, β-naphthyl, furyl, benzofuryl, benzothienyl, $H_2N(CH_2)_m-$, diphenylmethyl, $$R^4\overset{O}{\underset{\|}{C}}NH(CH_2)_m- \text{ or } R^4NH\overset{O}{\underset{\|}{C}}(CH_2)_m-;$$

$R^2$ is alkyl, alkyl-$S(O)_{0\text{-}2}(CH_2)_q-$, $R^5(CH_2)_kS(O)_{0\text{-}2}(CH_2)_q-$, alkyl-$O(CH_2)_q-$, $R^5(CH_2)_k\text{-}O(CH_2)_q-$, $R^5(CH_2)_q-$, $H_2N(CH_2)_q-$, cycloalkyl$(CH_2)_k-$, $R^{13}CONH(CH_2)_q-$, $R^{13}NHCO(CH_2)_q-$ or $R^6O\text{-}CO(CH_2)_q-$;

$R^3$ is $-OR^7$, $$-NR^8\underset{\underset{R^7}{|}}{},\ \text{NHCH}\underset{\underset{R^9}{|}}{\overset{\overset{R^7}{|}}{C}}NR^8\ \text{or}\ -\text{NHCH}\underset{\underset{R^9}{|}}{\overset{O}{\underset{\|}{C}}}OR^7;$$
(with carbonyl oxygens as shown)

$R^4$ and $R^{13}$ are independently hydrogen, alkyl or $Y^1-C_6H_4-$;

$R^5$ is $Y^2-C_6H_4-$, $Y^2-C_6H_4S-$, $Y^2-C_6H_4O-$, α-naphthyl, β-naphthyl, furyl, thienyl, benzofuryl, benzothienyl, indolyl or

[biphenyl structure with $Y^2$ and $X^1$ substituents]

provided that when $R^5$ is $Y^2-C_6H_4S-$ or $Y^2-C_6H_4O-$, k is 2 or 3;

$R^6$, $R^7$ and $R^8$ are independently H, alkyl, hydroxyalkyl, alkoxyalkyl, aminoalkyl, alkylaminoalkyl, dialkylaminoalkyl or arylalkyl, or $R^7$ and $R^8$ together with the nitrogen to which they are attached complete a 5-7 membered ring, wherein one of the 4-6 ring members comprising $R^7$ and $R^8$ may be a nitrogen atom, an alkyl-substituted nitrogen atom or an oxygen atom, and wherein the ring may be substituted on the ring carbon atoms with substituents chosen from alkyl and hydroxy groups;

$R^9$ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl, imidazolylalkyl, indolylalkyl or carbamoylalkyl;

n is 0-2;

m and k are independently 0-3;

q is 1-4;

X and $X^1$ are independently a bond, —O—, —S—, or —CH$_2$—;

Q is hydrogen or $R^{10}$CO—;

$R^{10}$ is alkyl, hydroxyalkyl, alkoxyalkyl, dialkylaminoalkyl, $Y^3$—C$_6$H$_4$-alkyl, alkoxy, $Y^3$—C$_6$H$_4$—, naphthyl, furyl, thienyl or pyridyl;

Y, $Y^1$, $Y^2$ and $Y^3$ independently represent one or more substituents selected from H, alkyl, cycloalkyl, alkoxy, OH, F, Cl, Br, CN, —CH$_2$NH$_2$, —CO$_2$H, —CO$_2$alkyl, —CONH$_2$ and phenyl;

$R^{1a}$ is Y—C$_6$H$_4$—, Y—C$_6$H$_4$S—, Y—C$_6$H$_4$O—,

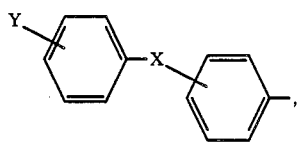

α-naphthyl, β-naphthyl, furyl, thienyl, benzofuryl, benzothienyl, H$_2$N(CH$_2$)$_m$—, diphenylmethyl,

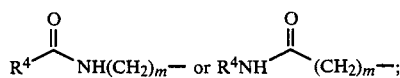

$R^{2a}$ $R^{5a}$(CH$_2$)$_k$S(O)$_{0-2}$(CH$_2$)$_q$—, $R^{5a}$(CH$_2$)$_k$-O(CH$_2$)$_q$—, $R^{5a}$(CH$_2$)$_q$—, or cycloalkyl-(CH$_2$)$_k$, and when $R^3$ is —NR$^7$R$^8$,

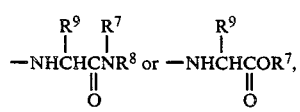

$R^{2a}$ may also be indolyl-(CH$_2$)$_q$—, $R^{13}$CONH(CH$_2$)$_q$—, $R^{13}$NHCO(CH$_2$)$_q$— or $R^6$OCO(CH$_2$)$_q$—;

$R^{3a}$ is

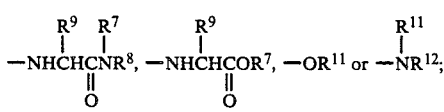

$R^{11}$ is hydroxyalkyl or substituted phenylalkyl wherein the phenyl group is substituted by one or more groups selected from alkyl, alkoxy, cycloalkyl and cyano; $R^{12}$ is H or selected from the same group as $R^{11}$; or $R^{11}$ and $R^{12}$ together with the nitrogen to which they are attached complete a 5-7 membered ring wherein one of the 4-6 ring members comprising $R^{11}$ and $R^{12}$ may be a nitrogen atom, an alkyl-substituted nitrogen atom or an oxygen atom, and wherein the ring may be substituted on the ring carbon atoms with substituents chosen from alkyl and hydroxy groups;

$R^{5a}$ is $Y^2$—C$_6$H$_4$ provided $Y^2$ is not H or OH, $Y^2$—C$_6$H$_4$S—, $Y^2$—C$_6$H$_4$O—, α-naphthyl, β-naphthyl, furyl, thienyl, benzofuryl, benzothienyl or

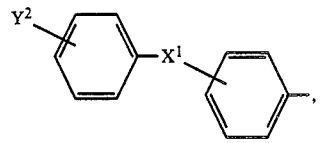

provided that when $R^{5a}$ is $Y^2$—C$_6$H$_4$—S— or $Y^2$—C$_6$H$_4$O—, k is 2 or 3;

and the pharmaceutically acceptable addition salt thereof.

As used herein the term "alkyl" means straight or branched alkyl chains of 1 to 6 carbon atoms, and "alkoxy" similarly refers to alkoxy groups having 1 to 6 carbon atoms. "Cycloalkyl" means cyclic alkyl groups of 3-6 carbon atoms.

"Aryl" means mono-cyclic or fused ring bicyclic aromatic groups having 5 to 10 ring members wherein 0-2 ring members may independently be nitrogen, oxygen or sulfer and wherein the ring members may be substituted by one to three substituents chosen from group Y defined above. Examples of aryl groups are phenyl, α-naphthyl, β-naphthyl, furyl, thienyl, benzofuryl, benzothienyl, indolyl and pyridyl.

"Halo" refers to fluorine, chlorine, bromine or iodine radicals. The term "poly", when used to describe substitution in a phenyl, alkylphenyl or alkoxyphenyl group, means 2 to 5 substituents.

Groups $R^3$ and $R^{3a}$ comprising the partial structure

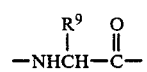

are derived from amino acids of formula

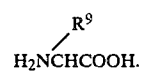

Examples of such amino acids are alanine, arginine, asparagine, aspartic acid, cysteine, glutamine, glutamic acid, glycine, histidine, isoleucine, leucine, lysine, methionine, phenylalanine, serine, threonine, tryptophan, tyrosine and valine.

Preferred embodiments of compounds of formula I are compounds wherein $R^2$ is alkyl, alkyl-S(O)$_{0-2}$(CH$_2$)$_q$—, $R^5$(CH$_2$)$_k$S(O)$_{0-2}$(CH$_2$)$_q$— or $R^5$(CH$_2$)$_q$—, wherein $R^5$, q and k are as defined above. Also preferred are compounds of formula I wherein $R^1$ is naphthyl, furyl, benzofuryl, benzothienyl, diphenylmethyl, aminoalkyl, Y—C$_6$H$_4$—X—C$_6$H$_4$—, $R^4$CONH(CH$_2$)$_m$— or $R^4$NHCO(CH$_2$)$_m$—, wherein Y, X, $R^4$ and m are as defined above. A third group of preferred compounds in that wherein $R^1$ is substituted phenyl. Still another group of preferred compounds of formula I is that wherein $R^3$ is —OR$^7$ or —NR$^7$R$^8$, wherein $R^7$ and $R^8$ are as defined above.

Preferred compounds of formula II are those wherein $R^{2a}$ is $R^5(CH_2)_kS(O)_{0-2}(CH_2)_q$— wherein $R^5$, q and k are as defined above. Also preferred are compounds of formula II wherein $R^{1a}$ is naphthyl, furyl, thienyl, benzofuryl, benzothienyl, diphenylmethyl, aminoalkyl, $Y—C_6H_4—X—C_6H_4—$, $R^4CONH(CH_2)_m$— or $R^4NHCO(CH_2)_m$— wherein Y, X, $R^4$ and m are as defined above. A third group of preferred compounds is that wherein $R^{1a}$ is $Y—C_6H_4$. Still another group of preferred compounds of formula II is that wherein $R^3$ is $—OR^7$ or $—NR^7R^8$, wherein $R^7$ and $R^8$ are as defined above.

Preferred compounds of formula III are those wherein $R^{3a}$ is $—NHCH_2CONH_2$, arylalkoxy or arylalkylamino. Also preferred are compounds of formula III wherein $R^{1a}$ is naphthyl, furyl, thienyl, benzofuryl, benzothienyl, diphenylmethyl, aminoalkyl, $Y—C_6H_4—X—C_6H_4—$, $R^4CONH(CH_2)_m$—or $R^4NHCO(CH_2)_m$— wherein Y, X, $R^4$ and m are as defined above. A third group of preferred compounds is that wherein $R^{1a}$ is substituted phenyl.

Preferred compounds of formulae I-III are those wherein Q is hydrogen or $R^{10}CO$— wherein $R^{10}$ is alkyl.

Compounds of this invention may, depending on the nature of functional groups, form addition salts with various inorganic and organic acids and bases. Such salts include salts prepared with organic and inorganic acids, e.g. HCl, HBr, $H_2SO_4$, $H_3PO_4$, methanesulfonic acid, toluenesulfonic acid, maleic acid, furmaric acid and camphorsulfonic acid. Salts prepared with bases include ammonium salts, alkali metal salts, e.g. sodium and potassium salts, and alkaline earth salts, e.g. calcium and magnesium salts.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formulae I–III have two or more asymmetrical carbon atoms and therefore include various stereoisomers. All stereoisomers are included within the scope of the present invention.

Compounds of the present invention may be prepared by using coupling reactions well known in the peptide art to join a 3-acetylthio-2-(substituted)-propionic acid of formula 1 with an amino acid ester of formula 2. The following reaction Scheme 1 is an example:

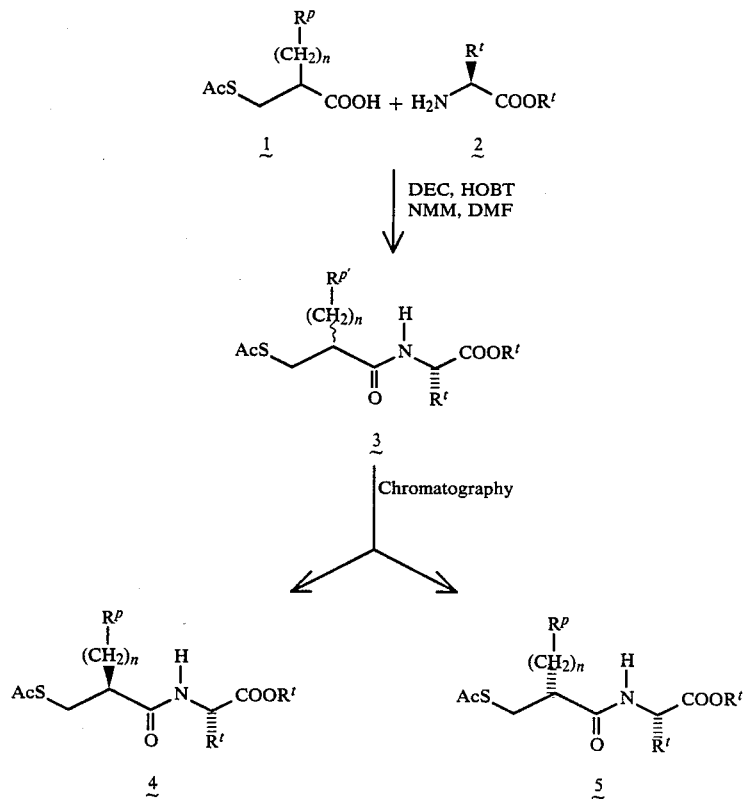

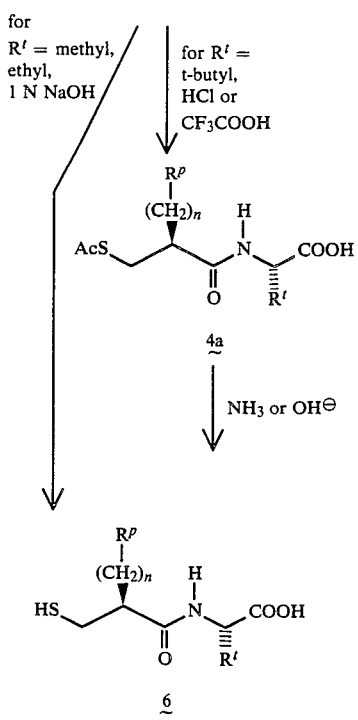
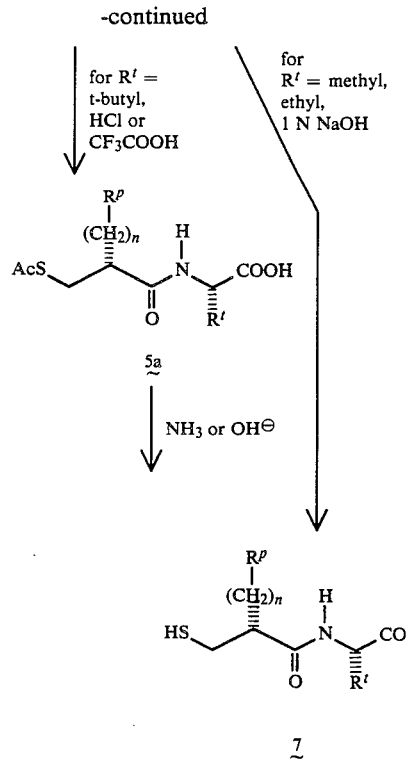

In the above scheme, $R^p=R^1$ and $R^{1a}$; $R^r=R^2$ and $R^{2a}$; $R^t$ is methyl, ethyl, t-butyl or aralkyl (e.g. benzyl); Ac is acetyl; n is 0–2; DEC is 1-(3-dimethylaminopropyl)-3-ethylcarbodiimide hydrochloride; HOBT is 1-hydroxybenzotriazole hydrate; NMM is N-methylmorpholine; and DMF is dimethylformamide.

As Scheme 1 shows, an amino acid ester of formula 2 and a 3-acetylthio propionic acid of formula 1 are reacted at room temperature in an inert solvent such as DMF in the presence of coupling agents such as DEC and HOBT in the presence of a base such as NMM. The resultant isomers are separated by chromatography and the isomers are deprotected at the acid and mercapto positions.

Alternatively, a propionic acid of formula 1 may be reacted with thionyl chloride to prepare the corresponding propionyl chloride, which may then be reacted with an amino acid ester of formula 2 or with the corresponding free acid 2a in an inert solvent such as acetonitrile in the presence of a base such as triethylamine to give isomers of formula 3, which may be separated as in Scheme 1. The following Scheme 2 is an example:

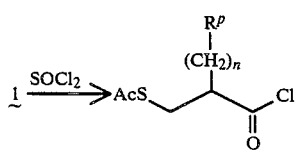

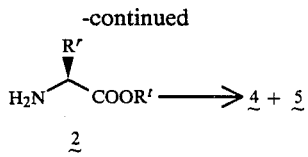

wherein n, Ac, $R^p$, $R^r$ and $R^t$ are as defined above, and wherein $R^t$ may also be hydrogen.

Compounds of formulae I–III wherein $R^3$ or $R^{3a}$ is $-NR^7R^8$ are prepared by coupling reactions as described above in Schemes 1 and 2 by replacing the amino acid ester 2 with an amide or substituted amide as shown in Scheme 3:

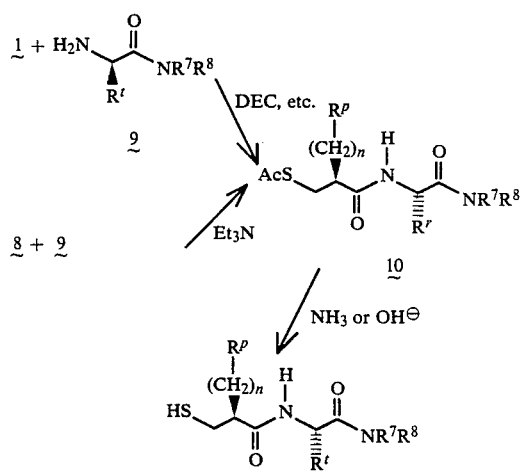

Alternatively, compounds of formulae I–III wherein $R^3$ or $R^{3a}$ is —$NR^7R^8$ may be prepared by coupling a propionyl chloride of formula 8 with an amino acid of formula 2a in the presence of a base and then coupling the desired —$NR^7R^8$ group to the carboxylic group using a typical peptide-coupling reaction. Scheme 4 shows an example of such a procedure:

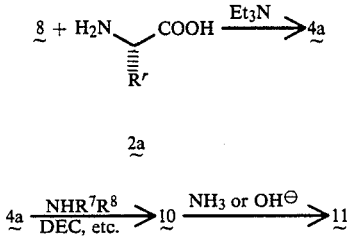

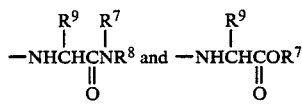

A third method for preparing compounds of formulae I–III wherein $R^3$ or $R^{3a}$ is —$NR^7R^8$ comprises reacting a propionic acid of formula 1 with an amino acid t-butyl ester of formula 2, removing the t-butyl ester and coupling the —$NR^7R^8$ group to the carboxylic acid group as above. Compounds wherein $R^3$ and $R^{3a}$ are $$-NHCHCNR^8 \text{ and } -NHCHCOR^7$$

(with $R^9$, $R^7$ substituents and C=O groups)

are prepared analogously to those wherein $R^3$ and $R^{3a}$ are —$NR^7R^8$.

Compounds wherein Q is $R^{10}CO$— may be prepared by known methods, for example by adding a mercaptoacid of formula $R^{10}$-COSH to an acrylic acid to obtain a thio-substituted propionic acid analogous to compounds of formula 1.

Starting materials of formulae 1 and 2 are known in the art or may be prepared by methods well known to those skilled in the art. Examples of typical preparations of starting materials and specific examples of compounds of formulae I–III are provided at the end of the specification.

A second aspect of the invention is the administration of a combination of an atrial natriuretic peptide and a compound of the following formula IV

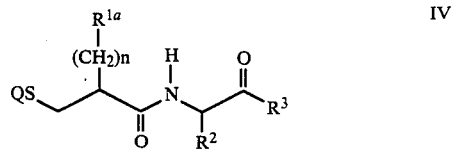

wherein n, $R^{1a}$, $R^2$, $R^3$ and Q are as defined above, for the treatment of hypertension. Compounds of formula IV have chiral centers and form addition salts as described above for compounds of formulae I–III, and may be prepared by similar methods.

As indicated by Needleman et al., a number of atrial peptides have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occurring atrial peptides also have been found to have comparable biological activity. Examples of atrial peptides contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence of each of the above wherein Met 12 is Ile. See Table 1 for a comparison of the peptides.

TABLE 1

HUMAN PEPTIDE

AP 33 .... Leu Ala Gly Pro Arg Ser Leu Arg Arg Ser Ser Cys Phe Gly Gly Arg Met* Asp Arg Ile Gly Ala Gln Ser Gly Leu Gly Cys Asn Ser Phe Arg Tyr
(disulfide bond between the two Cys residues)

AP 28 .... Ser————————————————————————————————Tyr

AP 26 .... Arg——————————————————————————Tyr

AP 25 .... Arg————————————————————————Tyr

AP 24 .... Ser————————————————————————Tyr

AP 23 .... Ser————————————————————Arg

AP 21 .... Ser————————————————Ser

*Ile in the rat peptide

We have found that the novel compounds Of the present invention are effective in treating congestive heart failure and various types of hypertension, particularly volume expanded hypertension. These novel compounds as well as other mercapto-acylamino acids known in the art have been found to enhance both the magnitude and duration of the antihypertensive and natriuretic effects of edogenous atrial natriuretic peptides. Administration of a combination of a mercapto-acylamino acid of formula IV and an exogenous atrial peptide is therefore particularly useful in treating hypertension.

In addition to the compound aspect, the present invention therefore also relates to treating hypertension with a mercapto-acylamino acid or with a mercapto-acylamino acid in combination with an atrial peptide, which methods comprise administering to a mammal in need of such treatment an antihypertensive effective amount of the mercapto-acylamino acid or the combination of a mercapto-acylamino acid and atrial peptide. The drug or combination of drugs is preferably administered in a pharmaceutically acceptable carrier, e.g. for oral or parenteral administration. The combination of drugs may be co-administered in a single composition, or components of the combination therapy may be administered separately. Where the components are administered separately, any convenient combination of dosage forms may be used, e.g. oral mercapto-acylamino acid/oral atrial peptide, oral mercapto-acylamino acid/parenteral atrial peptide, parenteral mercapto-acylamino acid/oral atrial peptide parenteral mercapto-acylamino acid/parenteral atrial peptide When the components of a combination of a mercapto-acylamino acid and an atrial peptide are administered separately, it is preferred that the mercapto-acylamino acid be administered first.

The present invention also relates to a pharmaceutical composition comprising a mercapto-acylamino acid for use in treating hypertension and to a pharmaceutical composition comprising both a mercapto-acylamino acid and an atrial peptide.

The antihypertensive effect of mercapto-acylamino acids was determined according to the following procedure: Male Sprague Dawley rats weighing 100-150 g were anesthetized with ether and the right kidney was removed. Three pellets containing Doc acetate (desoxycorticosterone acetate, DOCA, 25 mg/pellet) were implanted subcutaneously. Animals recovered from surgery, were maintained on normal rat chow and were allowed free acess to a fluid of 1% NaCl and 0.2% KCl instead of tap water for a period of 25-30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or mercapto-acylamino acid and blood pressure was monitored for the next 4 hours.

The antihypertensive effect of mercapto-acylamino acids in combination with atrial peptides was determined according to the following procedures:

Male spontaneously hypertensive rats (SHR), 16-18 weeks old, 270-350 g, were anesthetized with ether and the abdominal aorta was cannulated through the tail artery. The animals were then placed into restrainers to recover from anesthesia (in less than 10 min.) and remained inside throughout the experiments. Through a pressure transducer (Gould P23 series) analog blood pressure signals were registered on a Beckman 612 recorder. A Buxco digital computer was used to obtain mean arterial pressures. Patency of the arterial cannula was maintained with a continuous infusion of 5% dextrose at 0.2 ml/hr. Animals were allowed a 90-min equilibration period. The animals first underwent a challenge with an atrial peptide such as atriopeptin II (AP II) or AP28 30 µg/kg iv and at the end of 60 min. were treated with MC vehicle or a mercapto-acylamino acid subcutaneously. A second atrial peptide challenge was administered 15 min. later and blood pressure was monitored for the next 90 min.

The antihypertensive effect in SHR of mercapto-acylamino acids was determined as follows:

Animals were prepared for blood pressure measurement as described above. After stabilization, animals were dosed subcutaneously with test drugs or placebo and blood pressure was monitored for the next 4 hr.

The compositions of this invention comprise a mercapto-acylamino acid or a mercapto-acylamino acid and an atrial peptide in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily antihypertensive dose of the compound or combinations of this invention is as follows: for mercapto-acylamino acids alone the typical dosage is 1 to 100 mg/kg of mammalian weight per day administered in single or divided dosages; for the combination of mercapto-acylamino acid and an atrial peptide, the typical dosage is 1 to 100 mg of mercapto-acylamino acid/kg mammalian weight per day in single or divided dosages plus 0.001 to 0.1 mg atrial peptide/kg of mammalian weight per day, in single or divided dosages. The exact dose of any component or combination to be administered is determined by the attending clinician and is dependent on the potency of the compound administered, the age, weight, condition and response of the patient.

Generally, in treating humans having hypertension, the compounds or combinations of this invention may be administered to patients in a dosage range as follows: for treatment with mercapto-acylamino acids alone, about 10 to about 500 mg per dose given 1 to 4 times a day, giving a total daily dose of about 10 to 2000 mg per day; for the combination of mercapto-acylamino acid and atrial peptide, about 10 to about 500 mg mercapto-acylamino acid per dose given 1 to 4 times a day and about 0.001 to about 1 mg atrial peptide given 1 to 6 times a day (total daily dosage range of 10 to 2000 mg day and 0.001 to 6 mg/day, respectively). Where the components of a combination are administered separately, the number of doses of each component given per day may not necessarily be the same, e.g. where one component may have a greater duration of activity, and will therefore need to be administered less frequently.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol; starches such as cornstarch, tapioca starch and potato starch; ceullulose and derivatives such as sodium carboxymethyl cellulose, ethyl cellulose and methyl cellulose; calcium phosphates such as dicalcium phosphate and tricalcium phosphate; sodium sulfate; calcium sufate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene gylcol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Since the present invention relates to treatment of hypertension with a combination of active ingredients wherein said active ingredients may be administered separately, the invention also relates to combining separate pharmaceutical compositions in kit form. That is, a kit comprising a mercapto-acylamino acid and an atrial peptide in separate pharmaceutical compositions. The kit form is particularly advantageous when the separate components must be administered in different dosage forms (e.g. oral and parenteral) or are administered at different dosage intervals.

Following are descriptions of preparations of typical starting materials and examples of procedures for preparing compounds of formulae I–IV. Temperature designations, i.e. reaction conditions and melting points, are in °C.

PREPARATION 1

L-Cysteine Esters

Method 1: S-(4-Methylbenzyl)-L-Cysteine, Methyl Ester, Hydrochloride:

At room temperature, add thionyl chloride (2.8 ml, 2.2 equiv.) dropwise to N-t-butyloxycarbonyl-S-(4-methylbenzyl)-L-cysteine (5.0g) in methanol (500 ml) and heat the resulting mixture under reflux for 90 minutes. Cool the reaction mixture to room temperature and concentrate in vacuo to give the title compound, a white solid (4.31g), m.p. 158°–160°, $[\alpha]_D^{26} = -22.9°$ (MeOH).

By the same method, other amino acid esters are prepared:

S-Benzyl-D-cysteine ethyl ester hydrochloride, a while solid, m.p. 149°–151°, $[\alpha]_D^{26} = +15.5°$ (H₂O);

S-(4-Methoxybenzyl)-L-cysteine methyl ester hydrochloride, a white solid, m.p. 145°–6°, $[\alpha]_D^{26} = -23.2°$ (MeOH);

S-(3,4-Dimethylbenzyl)-L-cysteine ethyl ester hydrochloride, white solid, m.p. 161°–167°, $[\alpha]_D^{26} = -26.6°$ (MeOH); and S-t-Butyl-L-cysteine methyl ester, an oil.

Method 2: S-Phenethyl-L-Cysteine Ethyl Ester Hydrochloride:

Add thionyl chloride (2.0 ml) to absolute ethanol (25 ml) at 0°–5°. To this solution add S-phenethyl-L-cysteine (2.5 g, 1.11 mmole). Warm the resulting mixture to room temperature, and then heat at 60° for 5 hours. Concentrate the reaction mixture in vacuo, dissolve the resultant residue in dichloromethane (CH₂Cl₂), and concentrate the solution in vacuo. Dissolve the residue in absolute ethanol, treat with DARCO, filter and concentrate in vacuo to give the title compound, a white solid (2.90 g) m.p. 155°–156°, $[\alpha]_D^{26} = -1.5°$ (MeOH).

By the same method, other amino acid esters are prepared:

O-Benzyl-L-tyrosine methyl ester hydrochloride, a white solid, m.p. 189–190, $[\alpha]_D^{26} = +6.9°$ (MeOH);

S-Methyl-L-cysteine ethyl ester, an oil, $[\alpha]_D^{26} = +25.1°$ (MeOH);

S-Ethyl-L-cysteine ethyl ester hydrochloride, a white solid, m.p. 130°–3°$[\alpha]_D^{26} = -11.0°$ (MeOH); and Ethionine ethyl ester, hydrochloride, clear oil, $[\alpha]_D^{26} = +15.5°$ (MeOH).

PREPARATION 2

3-Acetylthio-2-(Arylmethyl)Propionic Acids

3-Acetylthio-2-(4-phenylbenzyl)propionic acid:

Step 1: 4-Biphenylmethylenemalonic acid: Heat 4-biphenyl carboxaldehyde (18.0 g, 9.89 mmole) and malonic acid (10.8 g, 10.4 mmole) in glacial acetic acid (6 ml) at approximately 100° for 2 hours. Cool the reaction mixture, dilute with dichloromethane and filter to give a white solid (8.76 g). Concentrate the filtrate, add malonic acid (1.5 g) and heat the resulting mixture at 100° for 2 hours. Cool the reaction mixture, dilute with CH₂Cl₂ and filter to give a white solid (3.44 g). Suspend the combined solids (12.20 g) in water and filter to give the title compound, a pale yellow solid (9.56 g), m.p. 208°–9° ↑.

By this method other aryl methylene malonic acids are prepared, for example:

β-Naphthylmethylene malonic acid, a white solid, m.p. 204°–205°.

Step 2: (4-Phenylbenzyl)malonic acid: Hydrogenate the product of Step 1 (9.50 g, 3.5 mmole) in ethyl acetate (200 ml) in the presence of 10% palladium-on-charcoal (0.80 g) at 50 psi for 3 hours. Filter and concentrate the reaction mixture in vacuo to give the title compound, a white solid (8.16 g) m.p. 180°–181°.

By this method other arylmethyl malonic acids are prepared, for example:

β-Naphthylmethyl malonic acid, a white solid, m.p. 150°–152°.

Step 3: 2-(4-Phenylbenzyl)acrylic acid: Treat a portion of the product of Step 2 (4.05 g, 1.50 mmole) in water (20 ml) at 0°–5° with 40% dimethylamine in water to pH 7–8. Add the remaining product of Step 2 (4.05 g, 1.50 mmole). After 15 minutes, add aqueous formaldehyde (10.0 ml, 38%). Slowly warm the resulting mixture to room temperature and stir for 18 hours. Filter the reaction mixture, wash the white solid with water, and suspend the solid in water (150 ml). Heat this suspension at 100° for 3 hours until the solution is almost clear. Cool the solution and add concentrated hydrochloric acid to pH 2 to give a white precipitate. Filter the mixture and dry the white solid. Dissolve this white solid in hot methanol, filter and concentrate in vacuo to give the title compound, a white solid (6.68 g) m.p. 168°–170°.

By this method other 2-(aryl)acrylic acids are prepared, for example:

2-(β-naphthylmethyl)acrylic acid, a white solid m.p. 83°–84°.

Step 4: 3-Acetylthio-2-(4-phenylbenzyl)propionic acid: Add thioacetic acid (8.0 ml) to the product of Step 3 (6.0 g, 2.77 mmole) in $CH_2Cl_2$ (30 ml) and ethyl acetate (100 ml) and stir the resulting mixture at room temperature for 72 hours. Concentrate the reaction mixture in vacuo. Dissolve the residue in toluene (100 ml), and concentrate in vacuo (3 times) to give a yellow oil (6.0 g). Chromatograph the oil on a column of silica gel (1.6L), eluting with $CH_2Cl_2$ (4L) $CH_2Cl_2$:methanol 1000:1 (3L), and 1000:5 (15L) to give the title compound, a white solid (3.44 g), m.p. 101°–103°.

By this method, other 3-acetylthio-2-(aryl methyl)propionic acids are prepared:

3-Acetylthio-2-(4-chlorobenzyl)propionic acid, an oil.
3-Acetylthio-2-(α-naphthylmethyl)propionic acid, a white solid, m.p. 94°–7°; and
3-Acetylthio-2-(β-naphthylmethyl)propionic acid, a white solid, m.p. 103°–106°.

PREPARATION 3

1-(α-Naphthylmethyl)Acrylic Acid

Step 1: Diethyl α-naphthylmethyl malonate: Add sodium metal (11.0 g, 0.478 mole) to absolute ethanol (650 ml) with cooling and stirring until the sodium is dissolved. Add diethyl malonate (75.6 g, 0.473 mole) over 15 minutes at room temperature. After 30 min., add α-bromomethylnaphthalene (100 g, 0.452 mole) in absolute ethanol (400 ml). Heat the resulting mixture under reflux for 5 hours. Keep at room temperature for 20 hours, and concentrate in vacuo. Partition the residue between water (500 ml) and diethyl ether (700 ml). Extract the diethyl ether solution with water (200 ml), and brine (200 ml), then dry the organic layer ($MgSO_4$) and concentrate in vacuo to give the title compound, an oil (133.7 g).

Step 2: 3-(1-Naphthyl)-2-ethoxycarbonylpropionic acid: To the product of Step 1 (133.7 g, 0.446 mole) in absolute ethanol (400 ml) add a solution of potassium hydroxide (24.9 g, 0.445 mole) in absolute ethanol (400 ml) and stir the resulting mixture at room temperature for 20 hours. Concentrate the reaction mixture in vacuo and partition the residue between ice water (1L) and diethyl ether (500 ml). Cool the aqueous solution to 0°–5° C. and acidify to approximately pH 2 with 2N hydrochloric acid, keeping the temperature at 0°–5°. Extract the mixture with diethyl ether, dry the organic layer ($MgSO_4$) and concentrate in vacuo to give the title compound, an oil (100 g).

Step 3: Ethyl 1-(α-naphthylmethyl)acrylate: Add to the product of Step 2 (100 g, 0.367 mole) and diethylamine (39 ml) a 37% aqueous solution of formaldehyde (38 ml) over 30 min. at 0°–5° C. with vigorous stirring. Stir the mixture at room temperature for 7 hours and then extract with diethyl ether (3×500 ml). Extract the organic layer with 2N hydrochloric acid (2×500 ml), saturated aqueous sodium bicarbonate solution (500 ml) and brine (500 ml). Dry the organic layer ($MgSO_4$) and concentrate in vacuo to give the title compound, an oil (58.6 g).

Step 4: 1-(α-Naphthylmethyl)acrylic acid: Treat the product of Step 3 (12.0 g, 50 mmole) in dioxane (50 ml) with 1N sodium hydroxide (60 ml) and stir the resulting mixture at room temperature for 18 hours. Concentrate the reaction mixture under nitrogen, dilute with water and extract with ethyl acetate. Cool the aqueous solution to 0°–5° and add concentrated hydrochloric acid slowly to pH 3–4 to give a white solid. Filter the reaction mixture, wash the resultant white solid with water and dry to give the title compound, a white solid (9.62 g), m.p. 115°–117°.

PREPARATION 4

L-Bishomophenylalanine t-Butyl Ester [(2S)-AMINO-5-PHENYLPENTANOIC ACID, t-BUTYL ESTER]

Step 1: 4-Benzoyl-2(S)-trifluoroacetamidobutyric acid: Heat at reflux for 3 hours a mixture of N-trifluoroacetyl-L-glutamic anhydride (18.0 g, 80 mmol) and $AlCl_3$ (23.5 g, 177 mmol) in dry benzene (400 ml). Allow to cool, treat with ice (400 ml), conc. HCl (100 ml), and ethylacetate (EtOAc) (400 ml). Dry the organic layer and concentrate to obtain the title compound as a brown crystalline solid (25 g).

Step 2: 5-Phenyl-2(S)-trifluoroacetamidopentanoic acid: Reduce the product of Step 1 (9.7 g) with Pearlman's catalyst (3.5 g) in EtOAc (75 ml) and ethanol (25 ml) at 50 psi $H_2$ for 3 hours. Filter, concentrate and wash the resultant residue with 3:1 hexane:diethyl ether to give the title compound (7.8 g).

Step 3: N-Trifluoroacetyl-L-bishomophenylalanine, t-butyl ester: Treat the product of Step 2 (11.3 g) with isobutylene (25 ml) and conc. $H_2SO_4$ (1.0 ml) in $CH_2Cl_2$ (100 ml) for 16 hours. Partition between diethyl ether and 1N $NaHCO_3$, dry, concentrate, and chromatograph the resultant residue on silica gel, eluting with 2:1 hexane:diethyl ether to obtain 11.3 g of the title compound as a colorless oil.

Step 4: L-Bishomophenylalanine, t-butyl ester, hydrochloride: To the product to Step 3 in EtOH (120 ml) add $NaBH_4$ (5.2 g) portionwise over 30 min. Stir another 1.5 hours, concentrate, and partition between diethyl ether and $H_2O$. Dry and concentrate to obtain an oil (8.1g). Treat with HCl:diethyl ether to give the hydrochloride salt of the title compound, white crystals (4.0 g), m.p. 161°–2°, $[\alpha]_D^{26} = +15.6°$ (MeOH, c=0.5).

PREPARATION 5

S-(4-Methylbenzyl)-L-Cysteine Amide

Step 1: N-t-Butyloxycarbonyl-S-(4-methylbenzyl)-L-cysteine amide: React N-t-butyloxycarbonyl-S-(4-methylbenzyl)-L-cysteine (6.50 g) with triethylamine (4.44 g, 6.16 ml) in tetrahydrofuran (THF). Cool the mixture to 0°–5°. Add ethyl chloroformate (4.77 g, 3.41 ml) in THF (5 ml) dropwise over 5 min. and stir the reaction mixture for 15 min. Add ammonium hydroxide (28%, 2.0 ml) in THF (5 ml) dropwise. Allow the reaction mixture to warm to room temperature and stir for 18 hr. Filter the reaction mixture and concentrate the filtrate in vacuo to give a pale yellow solid. Dissolve this solid in $CH_2Cl_2$ and extract with $H_2O$. Concentrate the dried ($MgSO_4$) $CH_2Cl_2$ solution in vacuo to give a pale yellow solid (6.41 g). Recrystallize this solid from EtOAc to give the title compound, a white solid (2.82 g), m.p. 140°–141°, $[\alpha]_D^{26} = -7.5°$ (MeOH).

Step 2: S-(4-Methylbenzyl)-L-cysteine amide: Treat the product of Step 1 (2.79 g) in $CH_2Cl_2$ (40 ml) with trifluoroacetic acid (10 ml) at room temperature for 18 hr. Concentrate the reaction mixture in vacuo. Dissolve the residue in $CH_2Cl_2$ and concentrate in vacuo (twice). Dissolve the white solid in EtOAc and extract with 10% sodium bicarbonate solution. Dry ($MgSO_4$) the EtOAc and concentrate in vacuo to give the title compound, a white solid (1.53 g) m.p. 94°-95°, $[\alpha]_D^{26}= -1.3°$ (MeOH).

PREPARATION 6

S-(4-Methylbenzyl)-L-Cysteine t-Butyl Ester

To a cold solution of isobutylene (50 ml) in dioxane (80 ml), add S-(4-methylbenzyl)-L-cysteine (5.0 g) and concentrated $H_2SO_4$ (10 ml). Seal the vessel, allow to warm to room temperature, and stir for 18 hr. Pour into 5% NaOH (500 ml), extract with $Et_2O$ (3×400 ml), dry ($MgSO_4$) and concentrate the $Et_2O$ in vacuo to give an oil. Treat the oil with HCl in $Et_2O$ to give the title compound, white needles (2.76 g) m.p. 218° (dec).

EXAMPLE 1

N-(2-Benxyl-3-Mercaptopropionyl)-S-(4-Methylbenzyl)-L-Cysteine (Isomers A and B)

Step 1: N-(3-Acetylthio-2-Benzylpropionyl)-S-(4-Methylbenzyl)-L-Cysteine Methyl Ester (Isomers A and B): Add S-(4-methylbenzyl)-L-cysteine methyl ester, hydrochloride (1.85 g, 0.77 mmole) to 3-acetylthio-2benzyl propionic acid (1.93 g, 0.81 mmole), DEC (1.46 g, 0.76 mmole), HOBT (1.18 g, 0.76 mmole) and NMM (2.30 g, 2.5 ml, 2.27 mmole) in DMF (20 ml) and stir the resulting mixture at room temperature for 20 hours. Concentrate the reaction mixture in vacuo and partition the residue between EtOAc and water. Concentrate the dried ($MgSO_4$) ethyl acetate solution in vacuo to give an amber oil (3.85 g). Chromatograph the oil on silica gel (Baker, 60–200 mesh) (1.5L) using EtOAc:hexane 4:21 as eluent to give Isomer A, white solid (0.64g), m.p. 101°-104°, $[\alpha]_D^{26}= -76.2°$ (MeOH); overlap Isomer A and Isomer B (0.40 g); and Isomer B, white solid (0.67 g), m.p. 52°-55° $[\alpha]_D^{26}= -4.9°$ (MeOH).

Step 2: N-(2-Benzyl-3-Mercaptopropionyl)-(S)-(4-Methylbenzyl)-L-Cysteine (Isomer B): Dissolve Isomer B (0.66 g, 1.6 mmole) in methanol (20 ml) under a nitrogen atmosphere, cool to 0°-5°, add 1N sodium hydroxide (4.8 ml), stir the mixture at 0°-5° for 6 hours and then keep at that temperature for 18 hours. Concentrate the reaction mixture under nitrogen, dilute the resultant oil with water (200 ml) and ethyl acetate (200 ml) and acidify to pH 2-4 with 1N hydrochloric acid. Dry ($MgSO_4$) the ethyl acetate solution and concentrate in vacuo to give the title compound (Isomer B), a viscous oil (0.45 g), $[\alpha]_D^{26}= -56.3°$ (MeOH).

Step 3: N-(2-Benzyl-3-Mercaptopropionyl)-(S)-4-Methylbenzyl)-L-Cysteine (Isomer A): By a procedure similar to that of Step 2 react Isomer A (0.63 g) and 1N sodium hydroxide (4.5 ml) to give the title compound (Isomer A), a viscous clear oil (0.165 g), $[\alpha]_D^{26}= -8.8°$ (MeOH).

In a similar manner, according to Example 1, Step 1, using the appropriate propionic acid, prepare:

N-[3-Acetylthio-2-(α-naphthylmethyl)propionyl]-S-(4-methylbenzyl)-L-cysteine ethyl ester, Isomer A, m.p. 71°-74°, $[\alpha]_D^{26}= -40.6°$ (MeOH);

N-[3-Acetylthio-2-(α-naphthylmethyl)propionyl]S-(4-methylbenzyl)-L-cysteine ethyl ester, Isomer B, m.p. 88°-90°, $[\alpha]_D^{26}= -58.8°$ (MeOH);

N-[3-Acetylthio-2(8-naphthylmethyl)propionyl]-S-(4-methylbenzyl)-L-cysteine ethyl ester, Isomer A, m.p. 74°-77°, $[\alpha]_D^{26}= -61.0°$ (MeOH);

N-[3-Acetylthio-2(β-naphthylmethyl)propionyl]-S-(4-methylbenzyl)-L-cysteine ethyl ester, Isomer B, m.p. 86°-88°, $[\alpha]_D^{26}= -20.7°$ (MeOH);

N-[3-Acetylthio-2-(4-chlorobenzyl)propionyl]-S- benzyl-L-cysteine ethyl ester (Isomer A), m.p. 89°-90°;

N-[3-Acetylthio-2-(4-chlorobenzyl)propionyl]-S-benzyl-L-cysteine ethyl ester (Isomer B), m.p. 103°-4°; and N-[3-Acetylthio-2-(4-chlorobenzyl)propionyl]-L-tryptophan methyl ester (Isomers A and B).

Using the procedure of Example 1, Step 2, treat the above 3-acetylthio compounds to obtain the following 3-mercaptopropionyl compounds:

N-[2-(α-Naphthylmethyl)-3-mercaptopropionyl]-S-(4-methylbenzyl)-L-cysteine Isomer A, m.p. 70°-75°, $[\alpha]_D^{26}= +18.3°$ (MeOH);

N-[2-(α-Naphthylmethyl)-3-mercaptopropionyl]-S-(4-methylbenzyl)-L-cysteine Isomer B, m.p. 48°-55°, $[\alpha]_D^{26}= -102.3°$ (MeOH);

N-[2-(β-Naphthylmethyl)-3-mercaptopropionyl]-S-(4-methylbenzyl)-L-cysteine, Isomer A, a white foam, $[\alpha]_D^{26} +9.9°$ (MeOH);

N-[2-(β-Naphthylmethyl)-3-mercaptopropionyl]-S-(4-methylbenzyl)-L-cysteine, Isomer B, a white foam, $[\beta]_D^{26}= -50.1°$ (MeOH);

N-[2-(4-chlorobenzyl)-3-mercaptopropionyl]-S-benzyl-L-cysteine (Isomer A), $[\alpha]_D^{26}= -3.0°$ (EtOH, c=1);

N-[2-(4-chlorobenzyl)-3-mercaptopropionyl]-S-benzyl-L-cysteine (Isomer B), $[\alpha]_D^{26}= -48.7°$ (EtOH, c=1);

N-[2-(4-chlorobenzyl)-3-mercaptopropionyl]-L-tryptophan (Isomer A), $[\alpha]_D^{26}= +18.1°$ (EtOH, c=0.5); and N-[2-(4-chlorobenzyl)-3-mercaptopropionyl]-L-tryptophan (Isomer B), $[\alpha]_D^{26}= -22.5°$ (EtOH, c=0.5).

EXAMPLE 2

N-(2-Benzyl-3-Mercaptopropionyl)-S-Benzyl-L-Cysteine (Isomers A and B)

Step 1: N-(3-Acetylthio-2-Benzylpropionyl)-S-Benzyl-L-Cysteine, Ethyl Ester (Isomers A and B): React S-benzyl-L-cysteine ethyl ester hydrochloride (1.38 g) and 3-acetylthio-2-benzyl propionic acid (1.19 g) in a procedure similar to that described in Example 1, Step 1 to give a yellow oil. Chromatograph the oil on silica gel (1.5L, 60–200 mesh) using $CH_2Cl_2$ ethyl acetate 98:2 as eluant to give Isomer A, white solid (0.49 g), m.p. 83°-5°, $[\alpha]_D^{26}= -73.5°$ (MeOH); overlap Isomer A and B (0.66 g); and Isomer B, white solid, m.p. 72°-4°, $[\alpha]_D^{26}= -9.4°$ (MeOH).

Step 2: Using the procedure described in Example 1, Step 2, separately treat the Isomers of Step 1 above to obtain Isomers A and B of the title compound: Isomer A, a colorless oil, $[\alpha]_D^{26} -2.1°$ (MeOH), and Isomer B, a colorless oil, $[\alpha]_D^{26}= -46.7°$ (MeOH).

EXAMPLE 3

N-(2-Benzyl-3-Mercaptopropionyl)-S-Benzyl-D-Cysteine (Isomers A and B)

Step 1: N-(3-Acetylthio-2-Benzylpropionyl)-S-Benzyl-D-Cysteine, Ethyl Ester (Isomers A and B): React S-benzyl-D-cysteine ethyl ester hydrochloride (2.05 g) and 3-acetylthio-2-benzylpropionic acid (1.77 g) in a manner similar to that described in Example 1, Step 1 to give a light amber oil. Place the oil on a column of silica gel (2L, 60–200 mesh) and elute with $CH_2Cl_2$:ethyl acetate 98:2 to give Isomer A, white solid (0.70 g), m.p. 84°-85°; $[\alpha]_D^{26}= +75 9°$ (MeOH); overlap Isomer A and Isomer B (0.85 g); and Isomer B, white solid (0.33 g), $[\alpha]_D^{26} = 0 + 15.6°$ (MeOH).

Step 2: Using the procedure described in Example 1, Step 2, separately treat the Isomers of Step 1 above to obtain Isomers A and B of the title compound: Isomer A, a colorless oil, $[\alpha]_D^{26} = +13.5°$ (MeOH); and Isomer B, a colorless oil, $[\alpha]_D^{26} = +38.2°$ (MeOH).

EXAMPLE 4

N-(2-Benzyl-3-Mercaptopropionyl)-S-(4-Methoxybenzyl)-L-Cysteine (Isomers A and B)

Step 1: N-(3-Acetylthio-2-Benzylpropionyl)-S-(4-Methoxybenzyl)-L-Cysteine Methyl Ester (Isomers A and B): React S-(4-methoxybenzyl)-L-cysteine methyl ester hydrochloride (1.85 g) and 3-acetylthio-2-benzylpropionic acid (1.95 g) in the manner described in Example 1, Step 1 to give an amber oil. Chromatograph this oil on a column of silica gel (2L, 60–200 mesh) and elute with ethyl acetate:hexane 5:20 to give Isomer A, a clear oil (0.63 g), $[\alpha]_D^{26} = -66.5°$ (MeOH), overlap Isomer A and Isomer B (0.28 g); and Isomer B, a clear oil (0.67 g), $[\alpha]_D^{26} = +3.0°$ (MeOH).

Step 2: Using the procedure described in Example 1, Step 2 separately treat the isomers of Step 1 above to obtain Isomers A and B of the title compound: Isomer A, a viscous oil, $[\alpha]_{Dphu\ 26} = -19.3°$ (MeOH); and Isomer B, a viscous oil, $[\alpha]_D^{26} = -44.2°$ (MeOH).

EXAMPLE 5

N-(2-Benzyl-3-Mercaptopropionyl)-S-(3,4-Dimethylbenzyl)-L-Cysteine (Isomers A and B)

Step 1: N-(3-Acetylthio-2-Benzylpropionyl)-S-(3,4-Dimethylbenzyl)-L-Cysteine Ethyl Ester (Isomers A and B): React S-(3,4-dimethylbenzyl)-L-cysteine ethyl ester hydrochloride (2.20 g) and 3-acetylthio-2-benzylpropionic acid (1.74 g) in the manner described in Example 1, Step 1 to give an amber oil. Place the oil on a column of silica gel (1L) and elute with ethyl acetate:hexane 25:170 (4L) and then methanol:hexane 25:170 to give a light orange oily solid. Repeat the chromatography to give Isomer A, a white solid (0.52 g), m.p. 89.5°–92.5°, $[\alpha]_D^{26} = -71.1°$ (MeOH) and Isomer B, a white solid (0.60 g), m.p. 51°–55°, $[\alpha]_D^{26} = -8.4°$ (MeOH).

Step 2: Using the procedure described in Example 1, Step 2, separately treat the Isomers of Step 1 above, to obtain Isomers A and B of the title compound: Isomer A, a clear viscous oil, $[\alpha]_D^{26} = -18.0°$ (MeOH); and Isomer B, a clear viscous oil, $[\alpha]_D^{26} = -56.5°$ (MeOH).

EXAMPLE 6

N-(2-Benzyl-3-Mercaptopropionyl)-S-Phenethyl-L-Cysteine (Isomers A and B)

Step 1: N-(3-Acetylthio-2-Benzylpropionyl)-S-Phenethyl-L-Cysteine Ethyl Ester, (Isomers A and B): React S-phenethyl-L-cysteine ethyl ester hydrochloride (2.85 g) and 3-acetylthio-2-benzylpropionic acid, (2.38 g) in a manner similar to that described in Example 1, Step 1 to give an amber oil. Chromatograph this oil on Prep 500 (2 silica gel cartridges) and elute with $CH_2Cl_2$ (4L) and then $CH_2Cl_2$ ethyl acetate 100:2 to give Isomer A, a white solid (1.32 g), m.p. 63°–64°, $[\alpha]_D^{26} = -51.2°$ (MeOH); overlap Isomer A and Isomer B (0.63 g); and Isomer B, white solid (1.14 g), m.p. 84°–86°, $[\alpha]_D^{26} = +5.3°$ (MeOH).

Step 2: Using the procedure described in Example 1, Step 2, separately treat Isomers A and B of Step 1 above to obtain Isomers A and B of the title compound. Isomer A, colorless oil, $[\alpha]_D^{26} = +4.8°$ (MeOH); and Isomer B, a colorless oil, $[\alpha]_D^{26} = -39.7°$ (MeOH).

EXAMPLE 7

N-(2-Benxyl-3-Mercaptopropionyl)-S-(t-Butyl)-L-Cysteine (Isomers A and B)

Step 1: N-(3-Acetylthio-2-Benzylpropionyl)-S-(t-Butyl)-L-Cysteine Methyl Ester (Isomers A and B): React S-(t-butyl)-L-cysteine methyl ester (2.32 g) and 3-acetylthio-2-benzylpropionic acid (3.22 g) in the manner described in Example 1, Step 1 to give an orange solid. Chromatograph this solid on a column of silica gel (2L, 60–200 mesh) and elute with ethyl acetate:hexane 3:17 to give Isomer A, a clear oil (1.09 g), $[\alpha]_D^{26} = -44.9°$ (MeOH); overlap Isomer A and Isomer B (0.52 g); and Isomer B, a clear oil (0.75 g), $[\alpha]_D^{26} = +8.3°$ (MeOH).

Step 2: Using the procedure described in Example 1, Step 2, separately treat the Isomers above to obtain Isomers A and B of the title compound; Isomer A, a clear viscous oil, $[\alpha]_D^{26} = +0.4°$ (MeOH), and Isomer B, a white solid, m.p. 68°–75.°, $[\alpha]_D^{26} = -32.3°$ (MeOH).

EXAMPLE 8

N-(2-Benzyl-3-Mercaptopropionyl)-L-Ethionine (Isomers A and B)

Step 1: N-(3-Acetylthio-2-Benzylpropionyl)-L-Ethionine Ethyl Ester (Isomers A and B): React L-Ethionine ethyl ester (3.51 g) and 3-acetylthio-2-benzylpropionic acid (4.37 g) in a manner similar to that described in Example 1, Step 1 to give a yellow residue. Chromatograph the yellow residue on the Waters Prep 500 (2 silica gel cartridges) and elute with ethyl acetate:hexane 2:18 (16L), then ethyl acetate:hexane 3:17. Repeat chromatography of the fractions using ethyl acetate:hexane as eluant to give Isomer A, a white solid (0.89 g), m.p. 84°–90°, $[\alpha]_D^{26} = -60.6°$ (MeOH) and Isomer B (0.82 g), m.p. 79°–84°, $[\alpha]_D^{26} = -0.3°$ (MeOH).

Step 2: Using the procedure described in Example 1, Step 2, separately treat the Isomers of Step 1 above to obtain Isomers A and B of the title compound; Isomer A, a milky viscous oil, $[\alpha]_D^{26} = -41.8°$ (MeOH); and Isomer B, a milky viscous oil, $[\alpha]_D^{26} = -66.0°$ (MeOH).

EXAMPLE 9

N-(2-Benzyl-3-Mercaptopropionyl)-O-Benzyl-L-Tyrosine (Isomers A and B)

Step 1: N-(3-Acetylthio-2-benzylpropionyl)-O-benzyl-L-tyrosine Methyl Ester (Isomers A and B): React O-benzyl-L-tryosine methyl ester hydrochloride (2.77 g) and 3-acetylthio-2-benzylpropionic acid (2.05 g) in a manner similar to that described in Example 1, Step 1 to give a yellow-orange oil. Chromatograph this oil on a column of silica gel (2.5L) and elute with $CH_2Cl_2$ ethyl acetate 98:2 to give Isomer A, a white solid (0.84 g) m.p. 108°–109°; $[\alpha]_D^{26} = -39.8°$ (MeOH); overlap Isomer A and Isomer B (0.80 g); and Isomer B, white solid (0.45 g), m.p. 92°–93°, $[\alpha]_D^{26} = +19.2°$ (MeOH).

Step 2: Using the procedure described in Example 1, Step 2, separately treat the Isomers of Step 1 above to obtain Isomers A and B of the title compound: Isomer A, an off-white solid, $[\alpha]_D^{26} = +4.8°$ (MeOH); and Isomer B, a viscous colorless oil $[\alpha]_D^{26} + 2.4°$ (MeOH).

EXAMPLE 10

N-(2-Benzyl-3-Mercaptopropionyl)-(S)-Bishomophenyl Alanine (Isomers A and B)

Step 1: N-(3-Acetylthio-2-Benzylpropionyl)-(S)-Bishomophenylalanine t-Butyl Ester (Isomers A and B): React (S)-bishomophenylalanine t-butyl ester hydrochloride (2.49 g) and 3-acetylthio-2-benzylpropionic acid (2.39 g) in the manner described in Example 1, Step 1 to give a yellow oil. Chromatograph this oil on Waters Prep 500 (2 silica gel cartridges) and elute with CH$_2$Cl$_2$ (4L) and then CH$_2$Cl$_2$:ethyl acetate 100:2 to give Isomer A, a colorless oil (0.99 g), $[\alpha]_D^{26} = -54.7°$ (MeOH), overlap Isomer A and Isomer B (0.62 g); and Isomer B, a colorless oil (0.79 g), $[\alpha]_D^{26} = +5.1°$ (MeOH).

Step 2: N-(3-Acetylthio-2-Benzylpropionyl)-(S)-Bishomophenylalanine (Isomer A and B): To Isomer A of the product of Step 1 (0.97 g, 0.21 mmole) in CH$_2$Cl$_2$ (10 ml) at 0°-5°, add dropwise trifluoroacetic acid (10 ml). Warm the resulting mixture to room temperature, stir for 18 hours, and concentrate in vacuo. Dissolve the residue in CH$_2$Cl$_2$ (10 ml) and concentrate in vacuo. Treat the residue with diethyl ether (10 ml) and concentrate in vacuo to give Isomer A of the title compound, a light amber oil (0.87 g), $[\alpha]_D^{26} = -43.0°$ (MeOH).

By this same method, convert Isomer B of Step 1 to N-(3-acetylthio-2-benzylpropionyl)-(S)-bishomophenylalanine Isomer B, a light amber oil, $[\alpha]_D^{26} = +19.6°$ (MeOH).

Step 3: N-(2-Benzyl-3-Mercaptopropionyl)-(S)-Bishomophenylalanine (Isomers A and B): Dissolve Isomer A of Step 2 in methanol (15 ml) at 0°-5° under a nitrogen atmosphere and treat with 1N sodium hydroxide (6.3 ml). Treat the resulting mixture as described in Example 1, Step 2, to give Isomer A of the title compound, a pale yellow viscous oil (0.69 g), $[\alpha]_D^{26} = -25.4°$ (MeOH).

By this same method, convert Isomer B of Step 2 to N-(2-benzyl-3-mercaptopropionyl)-(S)-bishomophenylalanine Isomer B, a pale yellow viscous oil, $[\alpha]_D^{26} = -50.0°$ (MeOH).

In a similar manner, substitute (S)-(4-methylbenzyl)-L-cysteine t-butyl ester (Preparation 6) for (S)-bishomophenylalanine in Example 10, Step 1 to obtain N-(3-acetylthio-2-benzylpropionyl)-(S)-(4-methylbenzyl)-L-cysteine t-butyl ester, Isomer A, $[\alpha]_D^{26} = -82.8°$ (MeOH); and N-(3-acetylthio-2-benzylpropionyl)-(S)-(4-methylbenzyl)-L-cysteine t-butyl ester, Isomer B, $[\alpha]_D^{26} = -23.5°$ (MeOH).

Treat the above esters in a manner similar to that described in Example 10, Step 2 to obtain N-(3-acetylthio-2-benzylpropionyl)-(S)-(4-methylbenzyl)-L-cysteine, Isomer A, $[\alpha]_D^{26} = -58.8°$ (MeOH); and N-(3-acetylthio-2-benzylpropionyl)-(S)-(4-methylbenzyl)-L-cysteine, Isomer B, $[\alpha]_D^{26} = -6.6°$ (MeOH).

EXAMPLE 11

N-[3-Mercapto-2(R,S)-Benzylpropionyl]-L-Methionine

Step 1: N-[3-Acetylthio-2(R,S)-Benzylpropionyl]-L-Methionine Methyl Ester: Add methionine methyl ester (2.00 g, 1.23 mmole) to 3-acetylthio-2-benzylpropionic acid (3.01 g, 1.26 mmole), DEC (2.34 g, 1.22 mmole), HOBT (1.88 g, 1.23 mmole) and NMM (2.34 g, 2.31 mmole) in DMF (12 ml), and treat the resulting mixture as described in Example 1, Step 1 to give an amber oil (4.36 g). Chromatograph the oil on a column of silica gel (1L 60–200 mesh) elute with CH$_2$Cl$_2$ (1L) and then CH$_2$Cl$_2$:ethyl acetate 99:1 to give the title compound, a clear oil (2.61 g), $[\alpha]_D^{26} = -38.9°$ (MeOH).

Step 2: N-[3-Mercapto-2(R,S)-Benzylpropionyl]-L-Methionine: Dissolve the product of Step 1 in methanol (20 ml) and treat with 1N NaOH (20.4 ml) as described in Example 1, Step 2 to give the title compound, a white solid, m.p. 132°-5°, $[\alpha]_D^{26} = -34.6°$ (MeOH).

Using the method of Example 11, Step 1, other N-[3-(R,S)-Acetylthio-2-benzylpropionyl]amino acid esters are prepared:

N-[3-Acetylthio-2(R,S)-benzylpropionyl]-S-methyl-L-cysteine ethyl ester, a clear oil, $[\alpha]_D^{26} = -25.9°$ (MeOH);

N-[3-Acetylthio-2(R,S)-benzylpropionyl]-S-trityl-L-cysteine methyl ester, an amber oil, $[\alpha]_D^{26} = +5.9°$ (MeOH); and N-[3-Acetylthio-2(R,S)-benzylpropionyl]-(S)-tryptophan methyl ester, a colorless oil, $[\alpha]_D^{26} = -14.7°$ (MeOH).

Using the procedure of Example 11, Step 2, convert the above 3-acetylthio comoounds to the following 3-mercaptopropionyl compounds:

N-[2(R,S)-Benzyl-3-mercaptopropionyl]-S-methyl-L-cysteine, a clear viscous oil, $[\alpha]_D^{26} = -31.1°$ (MeOH);

N-[2(R,S)-Benzyl-3-mercaptopropionyl]-S-trityl-L-cysteine, a white solid, $[\alpha]_D^{26} = +10.5°$ (MeOH); and N-[2(R,S)-Benzyl-3-mercaptopropionyl]-(S)-tryptophan, a white foam, m.p. 68°-69°, $[\alpha]_D^{26} = -0.5°$ (MeOH).

EXAMPLE 12

N-[2-(4-Phenylbenzyl)-3-Mercaptopropionyl]-S-(4-Methyl Benzyl)-L-Cysteine (Isomers A and B)

Step 1: 3-Acetylthio-2-(4-Phenylbenzyl)Propionyl Chloride: To 3-acetylthio-2-(4-phenylbenzyl)propionic acid (3.39 g, 10.8 mmole) in toluene (25 ml) add 1% DMF in toluene (2 drops) and thionyl chloride (1.2 ml, 1.65 g, 13.8 mmoles) and stir the resulting solution at room temperature for 18 hours. Concentrate the reaction mixture in vacuo, dissolve the residue in toluene (100 ml) and concentrate the solution in vacuo to give the title compound, a light brown oil (3.37 g).

Step 2: N-[3-Acetylthio-2-(4-Phenylbenzyl)Propionyl]-S(4-Methylbenzyl)-L-Cysteine (Isomers A and B): Add the acid chloride (3.37 g) from Step 1 in acetonitrile (25 ml) dropwise to S-(4-methylbenzyl)-L-cysteine hydrochloride (2.62 g, 10 mmol) in acetonitrile (30 ml), water (15 ml) and triethylamine (2.8 ml), and stir the resulting mixture at room temperature for 4 hours. Concentrate the reaction mixture in vacuo and partition the residue between ethyl acetate (700 ml) and water (2×200 ml) and then saturated sodium chloride solution (100 ml). Dry the ethyl acetate solution (MgSO$_4$) and concentrate in vacuo to give a brown solid. Chromatograph this solid on a column of silica gel (2L, 60°–200 mesh) and elute with CH$_2$Cl$_2$:methanol:glacial acetic acid (97.5:2.5:0.25) to give a white foam (2.45 g). Chromatograph this white foam on a column of silica gel (1.2L, 60–200 mesh) and elute with CH$_2$Cl$_2$:methanol:glacial acetic acid (97.5:2.5:0.25) to give the title compound, a white solid (1.04 g), m.p. 123°-125°, $[\alpha]_D^{26} = -45.5°$ (MeOH); overlap Isomers A and B (0.19 g); and Isomer B of the title compound, a white solid (0.86 g), m.p. 131°-135°, $[\alpha]_D^{26} = -7.1°$ (MeOH).

Step 3: N-[2-(4-Phenylhenzyl)-3-Mercaptopropionyl]-S-(4-Methylbenzyl)-L-Cysteine (Isomers A and B): Dissolve Isomer A of Step 2 in methanol saturated with ammonia (50 ml) at 0°-5° under a nitrogen atmosphere. After 35 minutes, bubble nitrogen through the reaction mixture. Dilute the reaction mixture with water and acidify to pH 2-4 with 1N hydrochloric acid. Extract the acidic solution with ethyl acetate, dry the organic layer (MgSO4) and concentrate in vacuo to give Isomer A of the title compound, a white solid (0.73 g). Purify Isomer A by flash chromatography on silica gel (Baker flash silica gel, 40 μM) (25 g) eluting with $CHCl_2:MeOH:gl.AcOH$, 97.5:2.5:0.25, to obtain a white solid (0.549 g), $[\alpha]_D^{26} = -2.2°$ (MeOH).

In a similar fashion, prepare Isomer B of the title comoound, a white solid, $[\alpha]_D^{26} = -62.2°$ (MeOH).

EXAMPLE 13

N-[2-Benzyl-3-Mercaptopropionyl]-L-Methionine Amide

Step 1: N-(3-Acetylthio-2-Benzylpropionyl)-L-Methionine Amide: In similar fashion to that described in Example 12, Step 2, convert L-methionine amide to N-(3-acetylthio-2-benzylpropionyl)-L-methionine amide. Recrystallize from hexane:$CH_2Cl_2$ to obtain a solid, m.p. 101°-3°. Chromatograph on silica gel with 4% methanol/$CH_2Cl_2$ to obtain Isomer A, m.p. 149°-51°, and Isomer B, m.p. 119°-21°.

Step 2: N-(2-Benzyl-3-Mercaptopropionyl)-L-Methionine Amide: Treat the 3-acetylthio compound (mixture of Isomer A and B) with NH3/MeOH for 4 hours as in Example 12, Step 3, to give the title compound, $[\alpha]_D^{26} = -53.5°$ (EtOH, c=1), a mixture of diastereomers.

In a similar manner to that described in Example 13, Step 1, substitute the appropriate acetylthio compounds and amides and separate by chromatography to obtain:
N-(3-Acetylthio-2-benzylpropionyl)-S-(4-methylbenzyl)-L-cysteine amide, Isomer A, $[\alpha]_D^{26} = -38.2°$ (MeOH);
N-(3-Acetylthio-2-benzylpropionyl)-S-(4-methylbenzyl)-L-cysteine amide, Isomer B, $[\alpha]_D^{26} = ]26D = -1.6°$ (MeOH);
N-[3-Acetylthio-2-(4-chlorobenzylpropionyl)]-L-methionine amide, Isomer A;
N-[3-Acetylthio-2-(4-chlorobenzylpropionyl)]-L-methionine amide, Isomer B, m.p. 166°-9°;

Treat the amides obtained above in a manner similar to that described in Example 13, Step 2 to obtain:
N-[2-(4-Chlorobenzyl)-3-mercaptopropionyl]-L-methionine amide, Isomer A, m.p. 194°, $[\alpha]_D^{26} = +1.2°$ (MeOH);
N-[2-(4-Chlorobenzyl)-3-mercaptopropionyl]-L-methionine amide, Isomer B, $[\alpha]_D^{26} = -65.2°$ (MeOH);
N-(2-Benzyl-3-mercaptopropionyl)-S-(4-methylbenzyl)-L-cysteine amide, Isomer A, m.o. 130°-2°, $[\alpha]_D^{26} = -4.2°$ (MeOH): and
N-(2-Benzyl-3-mercaptopropionyl)-S-(4-methylbenzyl)-L-cysteine amide, Isomer B, $[\alpha]_D^{26} = -29.0°$ (MeOH).

EXAMPLE 14

N-(3-Benzoylthio-2-Benzylpropionyl)-L-Methionine Amide

Prepare the R and S enantiomers of 3-benzoylthio-2-benzylpropionic acid according to the procedure described in U.S. Pat. No. 4,329,495, herein incorporated by reference.

In a manner similar to that described in Example 1, Step 1, condense each acid separately with L-methionine amide to obtain
N-(3(S)-benzoylthio-2-benzylpropionyl)-L-methionine amide, m.p. 178°-180°, $[\alpha]_D^{26} = -97.6°$ (MeOH); and
N-(3(R)-benzoylthio-2-benzylpropionyl)-L- C methionine amide, m.p. 145°-9°, $[\alpha]_D^{26} = +32.9°$ (CHC13)

EXAMPLE 15

N-[2-Benzyl-3-Mercaptipropionyl]-L-Aspartic Acid β-Benzyl Ester

In similar fashion to that described in Example 12, Step 2, convert L-aspartic acid β-benzyl ester to N(3-acetylthio-2-benzylpropionyl)-L-aspartic acid, β-benzyl ester.

Treat with NH3/MeOH as in Example 12, Step 3 to give the title compound, $[\alpha]_D^{26} = -5.7°$ (EtOH, c=0.5).

EXAMPLE 16

N-[N-(2-Benzyl-3-Mercaptopropionyl)-L-Phenylalanyl]-L-Alanine

Using the procedure of Example 1, convert L-phenylalanyl-L-alanine benzyl ester hydrochloride to N-(N-(3-acetylthio-2-benzylpropionyl)-L-phenylalanyl]-L-alanine, benzyl ester.

Treat with NaOH as in Example 1, Step 2 to give the crude title compound. React the product (0.62 g) with zinc powder (0.5 g) and 5N HCl (10ml) in 20ml MeOH for 1 hour. Concentrate the mixture, extract with $CH_2Cl_2$, dry, and remove the solvent to give the title compound, $[\alpha]_D^{26} = -23.1°$ (EtOH, c=0.5).

Use the same procedure to prepare N-(N-(2-benzyl-3-mercaptopropionyl)-L-phenylalanyl-L-leucine, $[\alpha]_D^{26} = -20.8°$ (EtOH, c=0.5).

EXAMPLE 17

N-[N-(2-Benzyl-3-Mercaptopropionyl)-L-Alanyl]-L-Proline

Step 1: N-[N-(3-Acetylthio-2-Benzylpropionyl)-L-Alanyl]-L-Proline: Using the procedure of Example 12, Step 2, convert L-alanyl-L- proline to N-[N-(3-acetylthio-2-benzylpropionyl)-L-alanyl]-L-proline, a white foam, $[\alpha]_D^{26} = -81.8°$ (MeOH).

Step 2: N-[N-(2-Benzyl-3-Mercaptopropionyl)-L-Alanyl]-L-Proline: Treat the product from Step 1 with methanol saturated with ammonia as described in Example 12, Step 3 (before chromatography). Treat the resultant residue with zinc powder as described in Example 17. Chromatograph the product on flash grade silica gel using $CH_2Cl_2$ MeOH:NH4OH (97.5:2.5:0.25) to give the title compound, $[\alpha]_D^{26} = -118.2°$ (MeOH).

We claim:

1. A compound having the structural formula

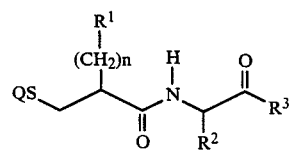

wherein

R is phenyl substituted by one to three substituents independently selected from alkyl, alkoxy, cycloalkyl, cyano and aminomethyl, y—C₆H₄S—, y—C₆H₄O—,

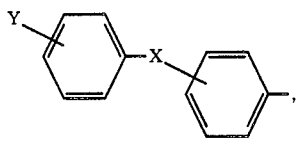

α-naphthyl, β-naphthyl, H₂N(CH₂)m, dipehnylmethyl,

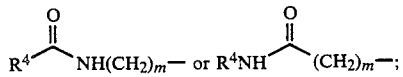

$R^2$ is alkyl, alkyl-S(O)$_{0-2}$(CH₂)$_q$—, R⁵(CH₂)kS(O)$_{0-2}$(CH₂)$_q$—, alkyl-O(CH₂)$_q$—, R⁵(CH₂)$_k$O(CH₂)$_q$—, R⁵(CH₂)$_q$, H₂N(CH₂)$_q$—, cycloalkyl(CH₂)$_k$—; R¹³CONH(CH₂)$_q$—,R¹³NHCO(CH₂)$_q$— or R⁶OCO(CH₂)$_q$—; R³ is —OR⁷, —NR⁷R⁸,

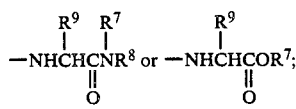

R⁴ and R¹³ are independently hydrogen, alkyl or Y¹—C₆H₄—;
R⁵ is Y²—C₆H₄S—, Y²—C₆H₄O—, β-naphthyl, β-naphthyyl, or

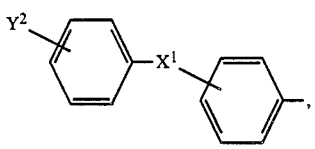

provided that when R⁵ is Y²—C₆H₄S— or Y²—C₆H₄O—, k is 2 or 3;
R⁶, R⁷ and R⁸ are independently H, alkyl, hydroxyalkyl, alkoxyalkyl, amioalkyl, alkylaminoalkyl, dialkylaminoalkyl, phenylalkyl, naphthylalkyl, Y-phenylalkyl, or Y-naphthylalkyl;
R⁹ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl, or carbamoylalkyl;
n is 0-2;
m and k are independently 0-3;
q is 1-4;
X and X¹ are independently a bond, —O—, —S—, or —CH₂—;
Q is hydrogen or R¹⁰CO—;
R¹⁰ is alkyl, hydroxyalkyl, aloxyalkyl, dialkylaminoalkyl, Y³—C₆H₄—alkyl, alkoxy, Y³—C₆H₄— or naphathyl;
Y, Y¹, Y² and Y³ independently represent one to three substituents selcted from H, alkyl, cycloalkyl, alkoxy, OH, F, CI, Br, CN, —CH₂NH₂, —CO₂H, —CO₂alkyl, —CONH₂ and phenyl wherein the term alkyl or and cycloalkyl is C₃ to C₆ each alkyl portion has 1-6 carbon atoms or a pharmaceutically acceptable addition salt thereof.

2. A compound of claim 1 wherein R² is alkyl, alkyl-S(O)$_{0-2}$(CH₂)$_q$—, R⁵(CH₂)$_k$S(O)$_{0-2}$(CH₂)$_q$— or R⁵(CH₂)$_q$—.

3. A compound of claim 1 wherein Q is hydrogen or R¹⁰CO— wherein R¹⁰ is alkyl.

4. A compound of claim 1 wherein R³ is —OR⁷ or 13 NR⁷R⁸.

5. A compound having the structural formula

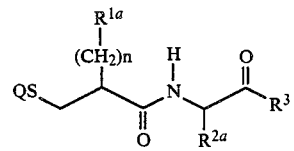

wherein
$R^{1a}$ is Y—C₆H₄—, Y—C₆H₄S—, Y—C₆H₄O—,

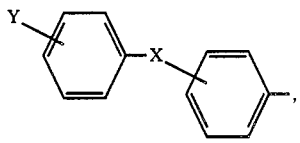

α-naphthyl, β-naphthyl, H₂N(CH₂)m—, diphneylmethyl,

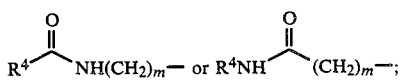

$R^{2a}$ is R⁵ᵃ(CH₂)$_k$S(O)$_{0-2}$(CH₂)$_q$—, R⁵ᵃ(CH₂)$_q$—, or cycloalkyl—(CH₂)$_k$, and when R³ is —NR⁷R⁸,

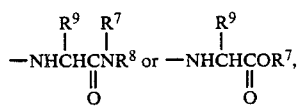

$R^{2a}$ may also be R¹³CONH(CH₂)$_q$—, R¹³NHCO(CH₂)$_q$— or R⁶OCO(CH₂)$_q$—; R³ is —OR⁷, —NR⁷R⁸,

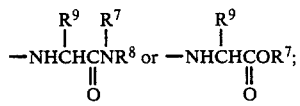

R⁴ and R¹³ are independently hydrogen, alkyl or Y¹—C₆H₄—;
$R^{5a}$ is Y²—C₆H₄— provided Y² is not H or OH, Y²₂C₆H₄S—, Y²—CH₄O—, α-naphthyl, β-naphthyl, or

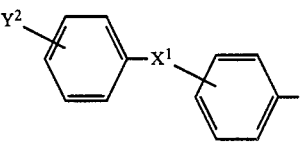

provided that when R⁵ᵃ is Y²—C₆H₄S— or Y²C₆H₄O—, k is 2 or 3;

$R^6$, $R^7$, and $R^8$ are independently H, alkyl, hydroxyalkyl, alkoxyalkyl, aminoalkyl, alkylaminoalkyl, dialkylaminoalkyl or phenylalkyl, naphthylalkyl, Y-phenylakyl, or Y-naphthylalkyl $R^9$ is hydrogen, alkyl, carboxyalkyl, mercaptoalkyl, alkylthioalkyl, aminoalkyl, hydroxyalkyl, phenylalkyl, hydroxyphenylakyl, guanidinoalkyl or carbamoylalkyl;

n is 0-2;

m and k are independently 0-3;

q is 1-4;

X and $X^1$ are independently a bond, —O—, —S—, or —CH$_2$—;

Q is hydrogen or $R^{10}$CO—;

$R^{10}$ is alkyl, hydroxyalkyl, alkoxyalkyl, dialkylaminoalkyl, $Y^3$—C$_6$H$_4$-alkyl, alkoxy, $Y^3$—C$_6$H$_4$— or naphthyl;

Y, $Y^1$, $Y^2$ and $Y^3$ independently represent one to three substituents selected from H, alkyl, cycloalkyl, alkoxy, OH, F, Cl, Br, CN, —CH$_2$NH$_2$, —CO$_2$H, —CO$_2$alkyl, —CONH$_2$ and phenyl wherein the term alkyl or and cycloalkyl is C$_3$ to C$_6$ each alkyl portion has 1-6 carbon atoms, or a pharmaceutically acceptable addition salt thereof.

6. A compound of claim 5 wherein $R^{2a}$ is $R^{5a}$(CH$_2$)$_k$S(O)$_{0-2}$(CH$_2$)$_q$—.

7. A compound of claim 5 wherein Q is hydrogen or $R^{10}$CO— wherein $R^{10}$ is alkyl.

8. A compound of claim 5 wherein $R^3$ is —OR$^7$ or —NR$^7$R$^8$.

9. A compound represented by the structural formula

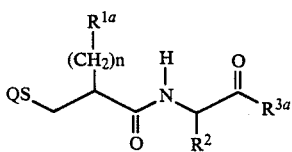

wherein
$R^{1a}$ is Y—C$_6$H$_4$—, Y—C$_6$H$_4$S—, Y—C$_6$H$_4$O—,

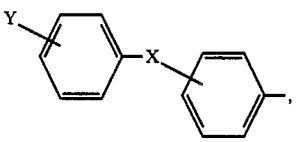

α-naphthyl, β-naphthyl, H$_2$N(CH$_2$)$_m$—, diphenylmethyl,

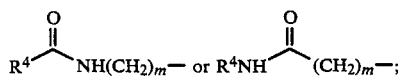

$R^2$ is alkyl, alkyl-S(O)$_{0-2}$(CH$_2$)$_q$—, $R^5$(CH$_2$)$_k$S(O)$_{0-2}$(CH$_2$)$_q$—, alkyl-O(CH$_2$)$_q$—, $R^5$(CH$_2$)$_k$O(CH$_2$)$_q$—, $R^5$(CH$_2$)$_q$—, H$_2$N(CH$_2$)$_q$—, cyloalkyl(CH$_2$)$_k$—, $R^{13}$CONH(CH$_2$)$_q$—, $R^{13}$NHCO(CH$_2$)$_q$— or $R^6$OCO(CH$_2$)$_q$—;

$R^{3a}$ is

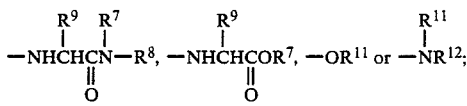

$R^4$ and $R^{13}$ are independently hydrogen, alkyl or $Y^1$—C$_6$H$_4$—;

$R^5$ is $Y^2$-C$_6$H$_4$, $Y^2$-C$_6$H$_4$S, $Y^2$-C$_6$H$_4$O—, α-naphthyl, β-naphthyl or

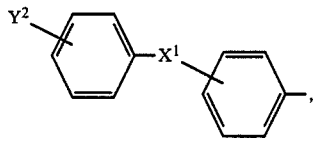

provided that when $R^5$ is $Y^2$—C$_6$H$_4$S— or $Y^2$C$_6$H$_4$O—, k is 2 or 3;

$R^6$, $R^7$ and $R^8$ are independently H, alkyl, hydroxyalkyl, alkoxyalkyl, aminoalkyl, alkylaminoalkyl, dialkylaminoalkyl phenylakyl, naphthylalkyl, Y—phenylkyl, or Y—naphthylalkyl;

$R^9$ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl or carbamoylakyl;

n is 0-2;

m and k are independently 0-3;

q is 1-4;

X and $X^1$ are independently a bond, —O—, —S, or —CH$_2$—;

Q is hydrogen or $R^{10}$CO—;

$R^{10}$ is alkyl, hydroxyalkyl, alkoxyalkyl, dialkylaminoalkyl, $Y^3$—C$_6$H$_4$-alkyl, alkoxy, $Y^3$—C$_6$H$_4$— or naphthyl;

$R^{11}$ is hydroxyalkyl, substituted phenylalkyl wherein the phenyl group is substituted by one or more groups selected from alkyl, alkxoy, cycloalkyl and cyano; $R^{12}$ is H or selected from the same group as $R^{11}$;

Y, $Y^1$, $Y^2$ and $Y^3$ independently represent one to three substituents selected from H, alkyl, cycloalkyl, alkoxy, OH, F, Cl, Dr, CN, —CH$_2$NH$_2$, —CO$_2$H, —CO$_2$alkyl, —CONH$_2$ and phenyl wherein the term alkyl or and cycloalkyl is C$_3$ to C$_6$ each alkyl portion has 1-6 carbon atoms, or a pharmaceutically acceptable addition salt thereof.

10. A compound of claim 9 wherein $R^{3a}$ is —NHCH$_2$CONH$_2$, arylalkoxy or arylalkylamino.

11. A compound of claim 9 wherein Q is hydrogen or $R^{10}$CO— wherein $R^{10}$ is alkyl.

12. A method for treating hypertension in mammals comprising administering to a mammal in need of such treatment an antihypertensive effective amount of a compound of claim 1.

13. A method for treating hypertension in mammals comprising administering to a mammal in need of such treatment an antihypertensive effective amount of a compound of claim 5.

14. A method for treating hypertension in mammals comprising administering to a mammal in need of such treatment an antihypertensive effective amount of a compound of claim 9.

15. An antihypertensive pharmaceutical composition comprising an antihypertensive amount of a compound of claim 1 in a pharmaceutically acceptable carrier.

16. An antihypertensive pharmaceutical composition comprising an antihypertensive amount of a compound of claim 5 in a pharmaceutically acceotable carrier.

17. An antihypertensive pharmaceutical composition comprising an antihypertensive amount of a compound of claim 9 in a pharmaceutically acceptable carrier.

* * * * *

UNITED STATES PATENT AND TRADEMARK OFFICE
CERTIFICATE OF CORRECTION

PATENT NO. : 4,801,609
DATED : January 31, 1989
INVENTOR(S) : Haslanger et al.

It is certified that error appears in the above-identified patent and that said Letters Patent is hereby corrected as shown below:

In column 27, line 1, delete "R" and insert — $R^1$ —.

In column 27, line 3, delete "$Y-C_6H_4S-$; $Y-C_6-$" and insert — $-Y-C_6H_4S-$; $Y-C_6-$ —.

In column 27, line 14, delete "$H_2N(CH_2)_m$, dipehnyl-" and insert — $H_2N(CH_2)_m-$, diphenyl- —.

In column 27, line 20, delete "$R^5(CH_2)kS)(O)-$" and insert — $R^5(CH_2)_kS(O)-$ —.

In column 27, line 23, delete "$R^5(CH_2)_q,$" and insert — $R^5(CH_2)_q-,$ —.

In column 27, lines 34-35, delete "β-naphthyl, β-naphthylyyl," and insert — α-naphthyl, β-naphthyl, —.

In column 27, line 47, delete "amioalkyl" and insert — aminoalkyl —.

In column 27, line 61, delete "aloxyalkyl" and insert — alkoxyalkyl —.

In column 27, line 63, delete "naphathyl" and insert — naphthyl —.

In column 27, line 67, after "phenyl", insert — ; —.

In column 27, line 68, after "alkyl or", delete — and cycloalkyl is $C_3$ to $C_6$ —.

UNITED STATES PATENT AND TRADEMARK OFFICE
CERTIFICATE OF CORRECTION

PATENT NO. : 4,801,609
DATED : January 31, 1989
INVENTOR(S) : Haslanger et al.

Page 2 of 3

It is certified that error appears in the above-identified patent and that said Letters Patent is hereby corrected as shown below:

In column 28, line 1, after "atoms", insert — and cycloalkyl is $C_3$ to $C_6$ —.

In column 28, line 8, delete "13".

In column 28, line 30, delete "diphneyl-" and insert — diphenyl —.

In column 28, line 36, before "$R^{5a}(CH_2)_q-$", insert — $R^{5a}(CH_2)_k-O(CH_2)_q-$, —.

In column 28, line 45, delete "$R^{13}$ $CONH(CH_2)_q-$" and insert — $R^{13}CONH(CH_2)_q-$ —.

In column 28, line 57, delete "$Y^2$," and insert — $Y^2-$ —.

In column 29, line 4, delete "phenylakyl" and insert — phenylalkyl —.

In column 29, line 8, delete "hydroxyphenylakyl" and insert — hydroxyphenylalkyl —.

In column 29, line 23, after "phenyl", insert — ; —.

In column 29, line 24, delete "and cycloalkyl is $C_3$ to $C_6$".

In column 29, line 25, after "atoms", insert — and cycloalkyl is $C_3$ to $C_6$ —.

In column 29, line 27, delete "$R^{5a}$" and insert — $R^{5a}-$ —.

In column 29, line 64, delete "cyloalk" and insert — cycloalk —.

UNITED STATES PATENT AND TRADEMARK OFFICE
CERTIFICATE OF CORRECTION

PATENT NO. : 4,801,609

DATED : January 31, 1989

INVENTOR(S) : Haslanger et al.

Page 3 of 3

It is certified that error appears in the above-identified patent and that said Letters Patent is hereby corrected as shown below:

In column 30, line 22, delete "phenylakyl" and insert — , phenylalkyl —.

In column 30, line 23, delete "nylkyl" and insert — nylalkyl —.

In column 30, line 26, delete "carbamoylakyl" and insert — carbamoylalkyl —.

In column 30, line 37, delete "alkxoy" and insert — alkoxy —.

In column 30, line 42, delete "Dr" and insert — Br —.

In column 30, line 43, after "phenyl", insert — ; —.

In column 30, line 44, delete "and cycloalkyl is $C_3$ to $C_6$".

In column 30, line 45, after "carbon atoms" insert — and cycloalkyl is $C_3$ to $C_6$ —.

Signed and Sealed this

Fifteenth Day of August, 1989

Attest:

DONALD J. QUIGG

Attesting Officer

Commissioner of Patents and Trademarks

UNITED STATES PATENT AND TRADEMARK OFFICE

Certificate

Patent Number: 4,801,609            Patented: January 31, 1989

On petition requesting issuance of a certificate of correction of inventorship pursuant to 35 U.S.C. 256, it has been found that the above-identified patent, through error and without any deceptive intent, improperly sets forth the inventorship. Accordingly, it is hereby certified that the correct inventorship of this patent is:
Martin F. Haslanger, Bernard R. Neustadt, Elizabeth M. Smith, Laura S. Lehman de Gaeta and Michael F. Czarniecki.

Signed and Sealed This Twenty-Sixth Day of December, 1989

MARY C. LEE

*Supervisory Patent Examiner*
*Patent Examing Group 120*
*Art Unit 121*
*Organic Chemistry*

REEXAMINATION CERTIFICATE (2126th)
United States Patent [19]
Haslanger et al.

[11] B1 4,801,609

[45] Certificate Issued Nov. 9, 1993

[54] MERCAPTO-ACYLAMINO ACID ANTIHYPERTENSIVES

[75] Inventors: Martin F. Haslanger, Ridgewood; Bernard R. Neustadt, West Orange; Elizabeth M. Smith, Verona, all of N.J.; Laura S. Lehman de Gaeta, La Jolla, Calif.; Michael F. Czarniecki, Watchung, N.J.

[73] Assignee: Schering Corporation, Kenilworth, N.J.

Reexamination Request:
No. 90/002,282, Feb. 14, 1991

Reexamination Certificate for:
Patent No.: 4,801,609
Issued: Jan. 31, 1989
Appl. No.: 32,153
Filed: Mar. 27, 1987

Certificate of Correction issued Dec. 26, 1989.

Certificate of Correction issued Aug. 15, 1989.

[51] Int. Cl.⁵ ............... A61K 31/095; A61K 31/16; A61K 31/265; A61K 31/275; C07C 321/06; C07C 321/16; C07C 327/28; C07C 327/30
[52] U.S. Cl. .................. 514/513; 514/506; 514/522; 514/529; 514/532; 514/540; 514/562; 558/254; 558/413; 558/414; 558/417; 564/153; 564/154; 562/426; 562/427; 562/432; 560/10; 560/16; 560/17; 560/18; 560/12; 560/13; 560/150; 560/153; 560/147

[58] Field of Search ............ 514/522, 513, 529, 532, 514/540, 562, 506; 558/254, 413, 414, 417; 564/153, 154, 155, 157, 158; 560/10, 16, 17, 18, 9, 13, 147, 149; 562/426, 427, 432

[56] References Cited

U.S. PATENT DOCUMENTS

| | | | |
|---|---|---|---|
| 4,053,651 | 10/1977 | Ondetti et al. | 558/254 |
| 4,105,776 | 8/1978 | Ondetti et al. | 424/274 |
| 4,228,077 | 10/1980 | Ondetti et al. | 260/326.14 T |
| 4,256,761 | 3/1981 | Suh et al. | 560/155 X |
| 4,329,495 | 5/1982 | Bindra | 564/153 |
| 4,339,600 | 7/1982 | Ondetti et al. | 562/426 |
| 4,401,677 | 4/1983 | Greenberg et al. | 564/153 |
| 4,500,467 | 2/1985 | Kubinyl et al. | 558/251 X |
| 4,513,009 | 4/1985 | Roques et al. | 558/254 |
| 4,740,499 | 4/1988 | Olins | 530/300 |

FOREIGN PATENT DOCUMENTS

| | | | |
|---|---|---|---|
| 0038046 | 10/1981 | European Pat. Off. | 558/254 |
| 0050800 | 5/1982 | European Pat. Off. | |
| 136883 | 4/1985 | European Pat. Off. | 564/153 |

OTHER PUBLICATIONS

Griffith, Ann. Rev. Biochem., 1986, pp. 855-878.
Needleman et al, N. Eng. J. Med., 314, 13 (1986) pp. 828-834.
Cantin et al, Scientific American, 254 (1986) pp. 76-81.
Smith, et al., Journal of Medicinal Chemistry, 1989, 32, pp. 1600-1606.

*Primary Examiner*—Joseph Paul Brust

[57] ABSTRACT

Novel mercapto-acylamino acids useful in the treatment of hypertension and combinations of mercapto-acylamino acids and atrial natriuretic peptides useful for treating hypertension are disclosed.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 3, 4, 5, 6, 7, 8, 12, 13, 15, 16 having been finally determined to be unpatentable, are cancelled.

Claim 9 is determined to be patentable as amended.

Claims 10, 11, 14 and 17, dependent on an amended claim, are determined to be patentable.

9. A compound represented by the structural formula wherein
$R^{1a}$ is $Y-C_6H_4-$, $Y-C_6H_4S-$, $Y-C_6H_4O-$, α-naphthyl, β-naphthyl, $H_2N(CH_2)_m-$, diphenylmethyl, $$\left[ R^4\overset{O}{\underset{\|}{C}}NH(CH_2)_m- \right] \text{ or } R^4NH\overset{O}{\underset{\|}{C}}(CH_2)_m-;$$

$R^2$ is alkyl, alkyl-$S(O)_{0-2}(CH_2)_q-$, $R^5(CH_2)_kS(O)_{0-2}(CH_2)_q-$, alkyl-$O(CH_2)_q-$, $R^5(CH_2)_kO(CH_2)_q-$, $R^5(CH_2)_q-$, $H_2N(CH_2)_q-$, cycloalkyl$(CH_2)_k-$, $R^{13}CONH(CH_2)_q-$, $R^{13}NHCO(CH_2)_q-$ or $R^6OCO(CH_2)_q-$;

$R^{3a}$ is $$-\underset{\underset{O}{\|}}{\overset{R^9}{\underset{|}{N}}HCH}\overset{R^7}{\underset{|}{C}}N-R^8, \quad -\underset{\underset{O}{\|}}{\overset{R^9}{\underset{|}{N}}HCHCOR^7}, \quad -OR^{11} \text{ or } -\overset{R^{11}}{\underset{|}{N}R^{12}}.$$

$R^4$ and $R^{13}$ are independently hydrogen, alkyl or $Y^1-C_6H_4-$;

$R^5$ is $Y^2-C_6H_4$, $Y^2-C_6H_4S$, $Y^2-C_6H_4O-$, α-naphthyl, β-naphthyl or provided that when $R^5$ is $Y^2-C_6H_4S-$ or $Y^2C_6H_4O-$, k is 2 or 3;

$R^6$, $R^7$ and $R^8$ are independently H, alkyl, hydroxyalkyl, alkoxyalkyl, aminoalkyl, alkylaminoalkyl, dialkylaminoalkyl, phenylalkyl, naphthylalkyl, Y—phenylalkyl, or Y—naphthylalkyl;

$R^9$ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl or carbamoylalkyl;

n is 0–2;
m and k are independently 0–3;
q is 1–4;
X and $X^1$ are independently a bond, —O—, —S, or —$CH_2$—;
Q is hydrogen or $R^{10}CO-$;
$R^{10}$ is alkyl, hydroxyalkyl, alkoxyalkyl, dialkylaminoalkyl, $Y^3-C_6H_4$-alkyl, alkoxy, $Y^3-C_6H_4-$ or naphthyl;
$R^{11}$ is hydroxyalkyl, substituted phenylalkyl wherein the phenyl group is substituted by one or more groups selected from alkyl, alkoxy, cycloalkyl and cyano; $R^{12}$ is H or selected from the same group as $R^{11}$;

Y, $Y^1$, $Y^2$ and $Y^3$ independently represent one to three substituents selected from H, alkyl, cycloalkyl, alkoxy, OH, F, Cl, Br, CN, —$CH_2NH_2$, —$CO_2H$, —$CO_2$alkyl, —$CONH_2$ and phenyl; wherein the term alkyl or each alkyl portion has 1–6 carbon atoms, and cycloalkyl is $C_3$ to $C_6$, or a pharmaceutically acceptable addition salt thereof.

* * * * *